US007311913B2

(12) United States Patent
Co et al.

(10) Patent No.: US 7,311,913 B2
(45) Date of Patent: *Dec. 25, 2007

(54) METHODS OF TREATING THROMBOTIC DISEASES WITH VON WILLEBRAND FACTOR SPECIFIC ANTIBODIES

(75) Inventors: Man Sung Co, Cupertino, CA (US); Maximiliano Vasquez, Palo Alto, CA (US)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/066,262

(22) Filed: Feb. 28, 2005

(65) Prior Publication Data

US 2005/0197494 A1 Sep. 8, 2005

Related U.S. Application Data

(63) Continuation of application No. 09/763,129, filed as application No. PCT/US99/16724 on Aug. 19, 1999, now abandoned.

(51) Int. Cl.
*A61K 39/395* (2006.01)

(52) U.S. Cl. .............................. 424/145.1; 424/133.1; 424/141.1; 530/387.3; 530/388.1; 530/388.25

(58) Field of Classification Search ..................... None
See application file for complete search history.

(56) References Cited

U.S. PATENT DOCUMENTS

| | | | | |
|---|---|---|---|---|
| 5,693,762 A * | 12/1997 | Queen et al. | ............ | 530/387.3 |
| 5,777,085 A | 7/1998 | Co et al. | | |
| 5,807,715 A | 9/1998 | Morrison et al. | | |
| 5,916,805 A * | 6/1999 | Nagano et al. | ............. | 435/337 |
| 6,228,360 B1 | 5/2001 | Co et al. | | |
| 6,280,731 B1 | 8/2001 | Nagano et al. | | |
| 6,613,328 B2 * | 9/2003 | Co et al. | ................. | 424/145.1 |
| 2003/0180293 A1 | 9/2003 | Co et al. | | |

FOREIGN PATENT DOCUMENTS

| | | |
|---|---|---|
| CN | 1174575 A | 2/1998 |
| EP | 0 795 608 | 10/1997 |
| WO | WO 9316185 A2 * | 8/1993 |
| WO | WO 9617078 A1 * | 6/1996 |

OTHER PUBLICATIONS

Janeway et al. Immunobiology, third edition, 1997, Garland Publishing Inc., pp. 3:7-3:9.*

Rudikoff et al. "Single amino acid substitutions altering antigen binding specificity", PNAS USA, 1982, 79:1979-1983.*

Amit et al. "Three-dimensional structure of an antigen-antibody complex at 2.8 angstrom reslolution" Science, 1986, 233:747-753.*

"The Statistics of Sequence Similarity Scores", downloaded from world wide web ncbi.nlm.nih.gov/BLAST/tutorial/Altschul-1.html on Nov. 4, 2005, 13 pages.*

Burton et al. "Human Antibody Effector Function" Advances in Immunology, 1992, vol. 51, pp. 1-84.*

Bergamaschini et al. "The role of IgG subclasses (IgG1 and/or IgG4) in the complement-activating capacity of immune complexes" J. Immunol. 1996, 156:1256-1261.*

Janeway et al., Immunobiology, third edition, 1997, pp. 3:1-3:38.*

Kageyma et al., Thrombosis Research, 2001, 101:395-404.*

Kageyama et al., Arterioscler Thromb Vasc Biol., 2002, 22:187-192.*

The Merck Manual of Diagnosis and Therapy, 17th edition, 1999, ed. Beers and Berkow, Merck Research Laboratories, pp. 1417-1427 and 1841-1845.*

Bleifeld W., Eur J Clin Pharmacol, 1990, 38 Suppl 1:s73-s76.*

Baumgartner et al., Annu Rev Med, 2005 56:249-272.*

Cooke, JP, Vasc Med, 1997, 2:227-230.*

Siegler, RL, Pediatr Clin North Am 1995, 42:1505-1529.*

Kelly, KJ, Semin Nephrol, 2006, 26:105-113.*

Caprioli et al., Curr Opin Crit Care, 2005, 5:487-492.*

Popma et al., Chest, 2004, 126:576s-599s.*

George et al., J Clin Apheresis, 1998, 13:120-125.*

Amirlak et al., Nephrology, 2006, 11:213-218.*

L.K. Jolliffe, "Humanized Antibodies: Enhancing Therapeutic Utility Through Antibody Engineering", Intern. Rev. Immunol., vol. 10, 1993, pp. 241-250.

Yamamoto, et al., "Anti-von willebrand factor antibody AJvW-2 specifically inhibits arterial but not venous thrombosis in the hamster," BLOOD, vol. 88, supplemental 10, part 1-2, p. 677, Abstract 172A.

Kageyama, et al., "Anti-thrombotic effects and bleeding risk of AJvW-2, a monocional antibody against human von willebrand factor," British Journal of Pharmacology, vol. 122, pp. 165-171.

Poletti, et al., "Prevention of arterial thrombosis using a novel heparin with enhanced antiplatelet activity and reduced anticoagulant activity," Journal of Vascular Surgery, vol. 26, No. 3, pp. 366-372.

A. Manheimer-Lory, et al., "Molecular Characteristics of Antibodies Bearing An Anti-DNA-Associated Idiotype," J. Exp. Med., vol. 174, Dec. 1991, pp. 1639-1652.

Fig. 9-11.12 of Day Hoff et al., Atlas of Protein Sequence and Structure, 5:89-99 (1972).

Jones, P. T., et al., "Replacing the Complementarity-Determining Regions in a Human Antibody with Those From a Mouse," Nature vol. 321, May 29, 1986, pp. 522-525.

Balint, R. F., et al., "Antibody Engineering by Parsimonious Mutagenesis," Gene, 137 (1993), pp. 109-118.

* cited by examiner

*Primary Examiner*—G. R. Ewoldt
*Assistant Examiner*—Michael Szperka
(74) *Attorney, Agent, or Firm*—Oblon, Spivak, McClelland, Maier & Neustadt, P.C.

(57) ABSTRACT

Anti-thrombotic agents containing humanized antibodies which bind to von Willebrand factor.

12 Claims, 5 Drawing Sheets

AJvW-2 heavy chain variable region sequence

```
                                   30                                      60
ATG GAT TTT GGG CTG ATT TTT TTT ATT GTT GCT CTT TTA AAA GGG GTC CAG TGT GAG GTG
 M   D   F   G   L   I   F   F   I   V   A   L   L   K   G   V   Q   C   E   V

                                   90                                     120
AAA CTT CTC GAG TCT GGA GGT GGC CTG GTG CAG ACT GGA GGA TCC CTG AAA CTC TCC TGT
 K   L   L   E   S   G   G   G   L   V   Q   T   G   G   S   L   K   L   S   C

                                  150                                     180
GCA GCC TCA GGA TTC GAT TTT AGT AGA TTC TGG ATG AGT TGG GTC CGG CAG GCT CCA GGG
 A   A   S   G   F   D   F   S   R   F   W   M   S   W   V   R   Q   A   P   G

                                  210                                     240
AAA GGG CTA GAA TGG ATT GGA GAA GTT AAT CCA GAT AAC AAT ACG ATG AAC TAT ACG CCA
 K   G   L   E   W   I   G   E   V   N   P   D   N   N   T   M   N   Y   T   P

                                  270                                     300
TCT CTA AAG GAT AAA TTC ATC ATC TCC AGA GAC AAC GCC AAA AAT ACG CTG TAC CTG CAA
 S   L   K   D   K   F   I   I   S   R   D   N   A   K   N   T   L   Y   L   Q

                                  330                                     360
ATG AGT CAA GTG AGA TCT GAG GAC ACA GCC CTT TAC TAC TGT GCA AGA CCT CCC TAC TAT
 M   S   Q   V   R   S   E   D   T   A   L   Y   Y   C   A   R   P   P   Y   Y

                                  390
GGT AGC TAC GGG GGG TTT GCT TAC TGG GGC CAA GGG ACT CTG GTC TCT GTC TCG CCA
 G   S   Y   G   G   F   A   Y   W   G   Q   G   T   L   V   S   V   S   P
```

FIG. 1a

AJvW-2 light chain variable region sequence

```
                                           30                                                   60
ATG AGT GTG CCC ACT CAG GTC CTG GGG TTG CTG CTG CTG TGG CTT ACA GAT GCC AGA TGT
 M   S   V   P   T   Q   V   L   G   L   L   L   L   W   L   T   D   A   R   C

                                           90                                                  120
GAC ATC CAG ATG ACT CAG TCT CCA GCC TCC CTA TCT GTA TCT GTG GGA GAA ACT GTC ACC
 D   I   Q   M   T   Q   S   P   A   S   L   S   V   S   V   G   E   T   V   T

                                          150                                                  180
ATC ACA TGT CGA GCA AGT GAG AAT ATT TAC AAT AAT TTA GCT TGG TAT CAG CAG AGA CAG
 I   T   C   R   A   S   E   N   I   Y   N   N   L   A   W   Y   Q   Q   R   Q

                                          210                                                  240
GGA AAA TCT CCT CAG CTC CTG GTC TAT GCT GCA ACA AAC TTA GCA GAT GGT GTG CCA TCA
 G   K   S   P   Q   L   L   V   Y   A   A   T   N   L   A   D   G   V   P   S

                                          270                                                  300
AGG TTC AGT GGC AGT GGA TCA GGC ACA CAG TAT TCC CTC AAG ATC GAC AGC CTG CAG TCT
 R   F   S   G   S   G   S   G   T   Q   Y   S   L   K   I   D   S   L   Q   S

                                          330                                                  360
GAA GAT TTT GGG AGT TAT TAC TGT CAA CAT TTG TGG ACT TCT CCG TAC ACG TTC GGA GGG
 E   D   F   G   S   Y   Y   C   Q   H   L   W   T   S   P   Y   T   F   G   G

GGG ACC AAG CTG GAA ATA AAA
 G   T   K   L   E   I   K
```

FIG. 1b

Humanized AJvW2 heavy chain variable region sequence

```
                                             30                                                60
ATG GAT TTT GGG CTG ATT TTT TTT ATT GTT GCT CTT TTA AAA GGG GTC CAG TGT GAG GTG
 M   D   F   G   L   I   F   F   I   V   A   L   L   K   G   V   Q   C   E   V

                                             90                                               120
CAA CTT GTC GAG TCT GGA GGT GGA CTA GTG CAG CCT GGA GGA TCA CTG AGA CTC TCC TGT
 Q   L   V   E   S   G   G   G   L   V   Q   P   G   G   S   L   R   L   S   C

                                            150                                               180
GCA GCC TCA GGA TTC GAT TTT AGT AGA TTC TGG ATG AGT TGG GTC CGG CAG GCT CCA GGG
 A   A   S   G   F   D   F   S   R   F   W   M   S   W   V   R   Q   A   P   G

                                            210                                               240
AAA GGG CTC GAG TGG ATT GGA GAA GTT AAT CCA GAT AAC AAT ACG ATG AAC TAT ACG CCA
 K   G   L   E   W   I   G   E   V   N   P   D   N   N   T   M   N   Y   T   P

                                            270                                               300
TCT CTA AAG GAT AAA TTC ACC ATC TCC AGA GAC AAC GCC AAA AAT ACG CTG TAC CTG CAA
 S   L   K   D   K   F   T   I   S   R   D   N   A   K   N   T   L   Y   L   Q

                                            330                                               360
ATG AAC TCA TTG AGA GCT GAG GAC ACG GCC GTT TAC TAC TGT GCA AGA CCT CCC TAC TAT
 M   N   S   L   R   A   E   D   T   A   V   Y   Y   C   A   R   P   P   Y   Y

                                            390
GGT AGC TAC GGG GGG TTT GCT TAC TGG GGC CAA GGG ACT CTG GTC ACC GTC TCC TCA
 G   S   Y   G   G   F   A   Y   W   G   Q   G   T   L   V   T   V   S   S
```

FIG. 2a

Humanized AJvW2 light chain variable region sequence

```
                                         30                                          60
ATG AGT GTG CCC ACT CAG GTC CTG GGG TTG CTG CTG CTG TGG CTT ACA GAT GCC AGA TGT
 M   S   V   P   T   Q   V   L   G   L   L   L   L   W   L   T   D   A   R   C

                                         90                                         120
GAC ATC CAG ATG ACT CAG TCT CCA TCC TCC CTA TCT GCA TCT GTG GGA GAC AGG GTC ACC
 D   I   Q   M   T   Q   S   P   S   S   L   S   A   S   V   G   D   R   V   T

                                        150                                         180
ATC ACA TGT CGA GCA AGT GAG AAT ATT TAC AAT AAT TTA GCT TGG TAT CAG CAG AAA CCG
 I   T   C   R   A   S   E   N   I   Y   N   N   L   A   W   Y   Q   Q   K   P

                                        210                                         240
GGA AAA GCT CCT AAG CTA CTA GTC TAT GCT GCA ACA AAC TTA GCA GAT GGT GTG CCA TCA
 G   K   A   P   K   L   L   V   Y   A   A   T   N   L   A   D   G   V   P   S

                                        270                                         300
AGG TTC AGT GGC AGT GGA TCA GGC ACA CAG TAT ACC CTC ACG ATC AGC AGC CTC CAG CCT
 R   F   S   G   S   G   S   G   T   Q   Y   T   L   T   I   S   S   L   Q   P

                                        330                                         360
GAG GAT TTT GCG ACT TAT TAC TGT CAA CAT TTG TGG ACT TCT CCG TAC ACG TTC GGA GGG
 E   D   F   A   T   Y   Y   C   Q   H   L   W   T   S   P   Y   T   F   G   G

GGG ACC AAG GTG GAA ATA AAA
 G   T   K   V   E   I   K
```

FIG. 2b

METHODS OF TREATING THROMBOTIC DISEASES WITH VON WILLEBRAND FACTOR SPECIFIC ANTIBODIES

CROSS-REFERENCE TO RELATED APPLICATIONS

The present application is a continuation application of U.S. Ser. No. 09/763,129, filed on May 16, 2001 now abandoned, which is a National Stage (371) of International Application PCT/US99/16724, filed on Aug. 19, 1999, which claims priority to U.S. application Ser. No. 09/136,315 (Now U.S. Pat. No. 6,228,360, issued May 8, 2001), filed on Aug. 19, 1998.

BACKGROUND OF THE INVENTION

1. Field of the Invention

Humanized monoclonal antibodies against human von Willebrand factor, cells which produce the antibodies, and antithrombotic agents containing the foregoing antibodies as the active ingredient.

2. Background of the Invention

When subendothelium tissue is exposed due to injury, platelets flowing through the bloodstream immediately adhere to the subendothelium. This event triggers a series of platelet activation processes including platelet aggregation and release of intracellular granules, after which a thrombus is formed and bleeding stops. Thrombus formation is necessary for the physiological hemostatic mechanism. However, the thrombus can cause a number of thrombotic diseases such as myocardial infarction, angina pectoris, cerebral infarction and cerebral thrombosis.

Many anti-thrombotic agents have been developed to treat thrombotic diseases. However, many conventional anti-thrombotic agents have low effectiveness in clinical applications and have low thrombus-specificity, causing hemorrhaging as a side effect.

An important protein which functions at the early stage of thrombus formation is von Willebrand factor ("vWF"), in blood plasma. Hemorrhagic legions associated with the occurrence of qualitative and quantitative changes in vWF are indications of von Willebrand disease ("vWD"). Several antibodies against vWF are known: NMC-4 disclosed by Fujimura et al, *J. Nara Med. Assoc.*, vol. 36, 662 (1985); RFF-VIIIRAG:1 disclosed by Tuddenham et al, *Blood*, vol. 177, no. 1, 113 (1992); and the monoclonal antibodies produced by hybridomas AJvW-1, AJvW-2, AJvW-3, and AJvW4 disclosed by Nagano et al, PCT/JP95/02435 (incorporated herein by reference).

The present invention provides humanized antibodies based on the antibodies produced by hybridoma AJvW-2. This murine monoclonal antibody is an effective inhibitor of the physiological activity of vWF and would be desirable to use for treating thrombotic diseases. Unfortunately, the use of murine monoclonal antibodies such as those from AJvW-2 have certain drawbacks in human treatment, particularly in repeated therapeutic regimens. And mouse monoclonal antibodies tend to have a short half-life in humans and lack other important immunoglobulin functional characteristics when used in humans. More importantly, murine monoclonal antibodies contain substantial amino acid sequences that are immunogenic when injected into human patients. Numerous studies have shown that, after injection of foreign antibodies, the immune response elicited in a patient against the injected antibody can be quite strong, eliminating the antibody's therapeutic effectiveness after the initial treatment. Moreover, if mouse or other antigenic (to humans) monoclonal antibodies are used to treat a human disease, then subsequent treatments with unrelated mouse antibodies may be ineffective or even dangerous due to cross-reactivity.

While the production of so-called "chimeric antibodies" (e.g., mouse variable regions joined to human constant regions) has proven somewhat successful, significant immunogenicity problems remain. (See, LoBuglio, A. F. et al., Proc. Natl. Acad. Sci. USA, 86, 4220-4224 (1989); M. N. Saleh et al., Human Antibod. Hybridomas e: 19 (1992)).

In general, producing human immunoglobulins reactive with von Willebrand factor with high affinity would be extremely difficult using typical human monoclonal antibody production techniques. Thus, there is a need for improved forms of humanized immunoglobulins specific for von Willebrand factor that are substantially non-immunogenic in humans, yet easily and economically produced in a manner suitable for therapeutic formulation and other uses. The present invention fulfills these and other needs.

SUMMARY OF THE INVENTION

An object of the invention is to provide humanized immunoglobulins, such as monoclonal antibodies, against von Willebrand factor, humanized forms of mouse antibody AJvW-2, polynucleotide sequences encoding the immunoglobulins; a method for producing the immunoglobulins; pharmaceutical compositions comprising the immunoglobulins as an active ingredient; a therapeutic agent for treating thrombotic diseases comprising the antibody as an active ingredient; and a method for treating such diseases.

BRIEF DESCRIPTION OF THE FIGURES

FIG. 1(*a*) is the heavy chain variable region sequence of AJvW-2, polynucleotide sequence=SEQ ID NO: 1 and protein sequence=SEQ ID NO: 2.

FIG. 1(*b*) is the light chain variable region sequence of AJvW-2, polynucleotide sequence=SEQ ID NO: 3 and protein sequence=SEQ ID NO: 4.

FIG. 2(*a*) is the heavy chain variable region sequence of a humanized AJvW-2, polynucleotide sequence=SEQ ID NO: 5 and protein sequence=SEQ ID NO: 6.

FIG. 2(*b*) is the light chain variable region sequence of a humanized AJvW-2, polynucleotide sequence=SEQ ID NO: 7 and protein sequence=SEQ ID NO: 8.

DETAILED DESCRIPTION OF THE INVENTION

Figure 3:
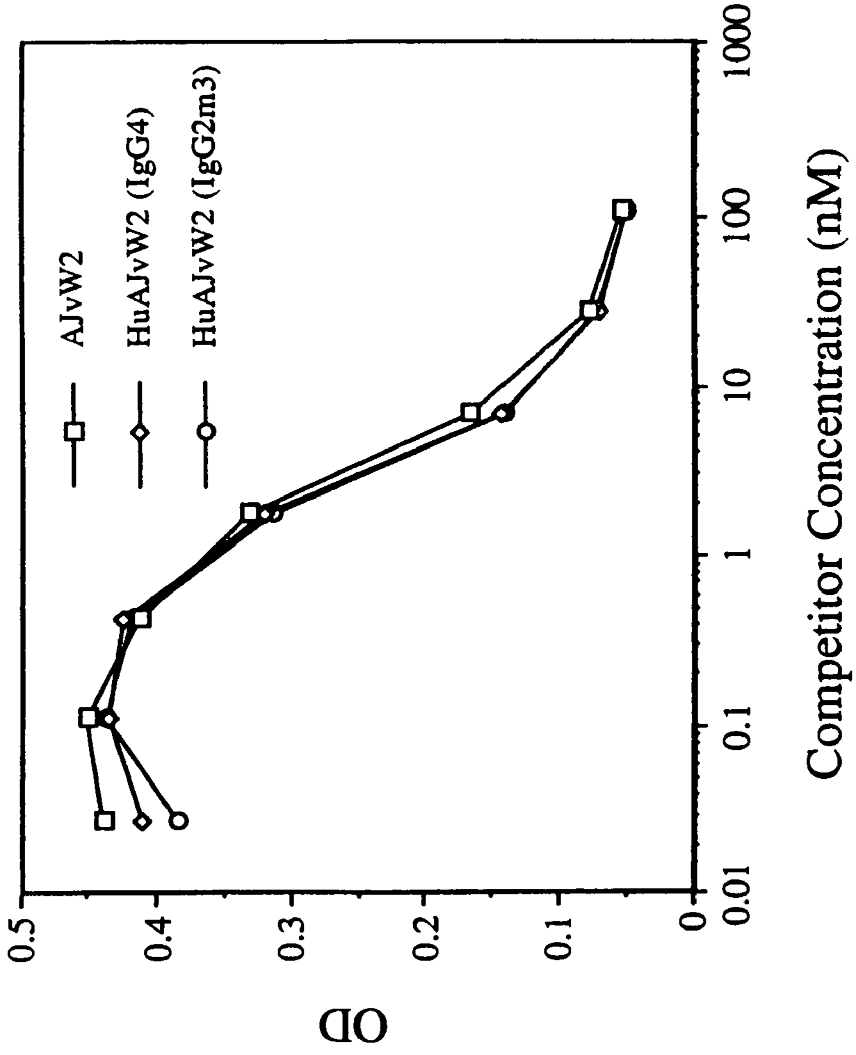
FIG. 3 is a graph of competitive binding properties of murine and humanized AjvW-2 antibodies (IgG4 and IgG2m3) to von Willebrand factor

In accordance with the present invention, humanized immunoglobulins specifically reactive with human von Willebrand factor are provided. These immunoglobulins, which have binding affinities to vWF of at least about $10^7$ $M^{-1}$ to $10^{10}$ $M^{-1}$, and preferably $10^8$ $M^{-1}$ to $10^{10}$ $M^{-1}$ or stronger, are capable of, e.g., inhibiting the binding of vWF to the GPIb protein in the presence of ristocetin or botrocetin.

The present invention provides novel anti-thrombotic compositions containing humanized immunoglobulins specifically capable of binding to the vWF of humans, and that inhibit RIPA (ristocetin-induced platelet aggregation), BIPA (botrocetin-induced platelet aggregation), and SIPA (shear stress-induced platelet aggregation) reactions of human platelets.

The immunoglobulins can have two pairs of light chain/heavy chain complexes, at least one chain comprising one or more mouse complementarity determining regions functionally joined to human framework region segments. For example, mouse complementarity determining regions, with or without additional naturally-associated mouse amino acid residues, can be introduced into human framework regions to produce humanized immunoglobulins capable of binding to the antigen at affinity levels stronger than about $10^7$ $M^{-1}$. These humanized immunoglobulins are capable of blocking the binding of the CDR-donating mouse monoclonal antibody to vWF (i.e., AJvW-2).

The immunoglobulins, including binding fragments and other derivatives thereof, of the present invention may be produced readily by a variety of recombinant DNA techniques, with ultimate expression in transfected cells, preferably immortalized eukaryotic cells, such as myeloma or hybridoma cells. Polynucleotides comprising a first sequence coding for humanized immunoglobulin framework regions and a second sequence set coding for the desired immunoglobulin complementarity determining regions can be produced synthetically or by combining appropriate cDNA and genomic DNA segments.

The humanized immunoglobulins may be used in substantially pure form in thrombolytic therapy, that is, removal of preformed intravascular fibrin occulsions. They are also used for prevention and treatment of athelosclerosis and restenosis after vascular intervention. They are used for treating a patient having or at risk of a thrombotic disease such as stroke, transient ischemic attacks, unstable angina, acute myocardial infarction, angina pectoris, peripheral vascular disease, deep vein thrombosis and hemolytic uremic syndrome comprising hemolytic anemia, acute renal failure and thrombotic thrombocytopenic purpura. They are also used for preventing ischemic complications caused by acute and subacute thrombosis or restenosis after endovascular intervention such as PTCA, stent, atherectomy and coronary bypass surgery and preventing ischemic complications caused by reocclusion after thrombolytic treatment in acute myocardial infarction as an adjunctive therapy.

The humanized immunoglobulins or their complexes can be prepared in a pharmaceutically accepted dosage form, which will vary depending on the mode of administration.

The humanized immunoglobulins have a human framework and one or more complementarity determining regions (CDR's) from immunoglobulin AJvW-2. However, the CDRs from other antibodies that compete with AJvW-2, block the binding of vWF to the GPIb protein in the presence of ristocetin or botrocetin, and/or bind to the same epitope on vWF as AJvW-2 does may also be used. The present immunoglobulins can be produced economically in large quantities, and find use, for example, in the treatment of thrombotic diseases in human patients by a variety of techniques.

The basic antibody structural unit is known to comprise a tetramer. Each tetramer is composed of two identical pairs of polypeptide chains, each pair having one "light" (about 25 kD) and one "heavy" (about 50-70 kD) chain. The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See, *Fundamental Immunology*, Paul, W., Ed., Chapter 7, pgs. 131-166, Raven Press, N.Y. (1984), which is incorporated herein by reference.)

The variable regions of each light/heavy chain pair form the antibody binding site. The chains all exhibit the same general structure of relatively conserved framework regions joined by three hypervariable regions, also called Complementarity Determining Regions or CDR's (see, "Sequences of Proteins of Immunological Interest," Kabat, E., et al., U.S. Department of Health and Human Services, (1987); and Chothia and Lesk, J. Mol. Biol., 196, 901-917 (1987), which are incorporated herein by reference). The CDR's from the two chains of each pair are aligned by the framework regions, enabling binding to a specific epitope.

As used herein, the term "immunoglobulin" refers to a protein consisting of one or more polypeptides substantially encoded by immunoglobulin genes. The recognized immunoglobulin genes include the kappa, lambda, alpha, gamma, delta, epsilon and mu constant region genes, as well as the myriad immunoglobulin variable region genes. The immunoglobulins may exist in a variety of forms besides antibodies; including, for example, Fv, Fab, and $F(ab')_2$ as well as bifunctional hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science 242, 423-426 (1988), which are incorporated herein by reference). (See, Hood et al., *Immunology*, Benjamin, N.Y., $2^{nd}$ ed. (1984), Harlow and Lane, *Antibodies. A Laboratory Manual*, Cold Spring Harbor Laboratory (1988) and Hunkapiller and Hood, Nature, 323, 15-16 (1986), which are incorporated herein by reference.).

Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as $\gamma_1$ and $\gamma_3$. A typical therapeutic chimeric antibody is thus a hybrid protein consisting of the V or antigen-binding domain from a mouse antibody and the C or effector domain from a human antibody, although other mammalian species may be used.

As used herein, the term "framework region" refers to those portions of immunoglobulin light and heavy chain variable regions that are relatively conserved (i.e., other than the CDR's) among different immunoglobulins in a single species, as defined by Kabat, et al., op. cit. As used herein, a "human framework region" is a framework region that is substantially identical (about 85% or more) to the framework region of a naturally occurring human antibody.

As used herein, the term "humanized immunoglobulin" refers to an immunoglobulin comprising a human framework, at least one CDR from a non-human antibody, and in which any constant region present is substantially identical to a human immunoglobulin constant region, i.e., at least about 85-90%, preferably at least 95% identical. Hence, all parts of a humanized immunoglobulin, except possibly the CDR's, are substantially identical to corresponding parts of one or more native human immunoglobulin sequences. For example, a humanized immunoglobulin would not encompass a chimeric mouse variable region/human constant region antibody.

Humanized antibodies have at least three potential advantages over mouse and in some cases chimeric antibodies for use in human therapy:

1. Because the effector portion is human, it may interact better with the other parts of the human immune system (e.g., destroy the target cells more efficiently by complement-dependent cytotoxicity (CDC) or antibody-dependent cellular cytotoxicity (ADCC)).

2. The human immune system should not recognize the framework or C region of the humanized antibody as foreign, and therefore the antibody response against such an injected antibody should be less than against a totally foreign mouse antibody or a partially foreign chimeric antibody.

3. Injected mouse antibodies have been reported to have a half-life in the human circulation much shorter than the half-life of normal antibodies (Shaw, D. et al., J. Immunol, 138, 4534-4538 (1987)). Injected humanized antibodies will presumably have a half-life essentially identical to naturally occurring human antibodies, allowing smaller and less frequent doses to be given.

The present invention relates to recombinant polynucleotides encoding the heavy and/or light chain CDR's from immunoglobulins capable of binding vWF in the manner of monoclonal antibody AJvW-2. The polynucleotides encoding these regions will typically be joined to polynucleotides encoding appropriate human framework regions. As to the human framework region, a framework or variable region amino acid sequence of a CDR-providing non-human immunoglobulin is compared with corresponding sequences in a human immunoglobulin sequence collection, and a sequence having high homology is selected. Exemplary polynucleotides, which on expression code for the polypeptide chains comprising the heavy and light chain CDR's of monoclonal antibody AJvW-2 are included in FIGS. 1 and 2. Due to codon degeneracy and non-critical amino-acid substitutions, other polynucleotide sequences can be readily substituted for the sequences in FIGS. 1 and 2, as described below.

The design of humanized immunoglobulins may be carried out as follows. When an amino acid falls under one of the following categories, the framework amino acid of a human immunoglobulin to be used (acceptor immunoglobulin) is replaced by a framework amino acid from a CDR-providing non-human immunoglobulin (donor immunoglobulin):

(a) the amino acid in the human framework region of the acceptor immunoglobulin is unusual for human immunoglobulins at that position, whereas the corresponding amino acid in the donor immunoglobulin is typical for human immunoglobulins at that position;

(b) the position of the amino acid is immediately adjacent to one of the CDR's; or (c) the amino acid is capable of interacting with the CDRs in a tertiary structure immunoglobulin model (see, Queen et al., op. cit., and Co et al., Proc. Natl. Acad. Sci. USA 88, 2869 (1991), respectively, both of which are incorporated herein by reference).

For a detailed description of the production of humanized immunoglobulins see, Queen et al., op. cit., and Co et al., op. cit.

The polynucleotides will typically further include an expression control polynucleotide sequence operably linked to the humanized immunoglobulin coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the light chains, heavy chains, light/heavy chain dimers or intact antibodies, binding fragments or other immunoglobulin forms may follow.

The nucleic acid sequences of the present invention capable of ultimately expressing the desired humanized antibodies can be formed from a variety of different polynucleotides (genomic or cDNA, RNA, synthetic oligonucleotides, etc.) and components (e.g., V, J, D, and C regions), as well as by a variety of different techniques. Joining appropriate genomic and synthetic sequences is presently the most common method of production, but cDNA sequences may also be utilized (see, European Patent Publication No. 0239400 and Riechmann, L. et al., Nature, 332, 323-327 (1988), both of which are incorporated herein by reference.)

Human constant region DNA sequences can be isolated in accordance with well known procedures from a variety of human cells, but preferably immortalized B-cells (see, Kabat op. cit. and WP 87/02671). The CDR's for producing the immunoglobulins of the present invention will be similarly derived from monoclonal antibodies capable of binding to vFW in the manner of AJvW-2 and produced in any convenient mammalian source, including, mice, rats, rabbits, or other vertebrate capable of producing such antibodies, by well known methods. Suitable source cells for the polynucleotide sequences and host cells for immunoglobulin expression and secretion can be obtained from a number of sources, such as the American Type Culture Collection (*Catalogue of Cell Lines and Hybridomas*, Fifth edition (1985) Rockville, Md., U.S.A., which is incorporated herein by reference).

In addition to the humanized immunoglobulins specifically described herein, other "substantially homologous" modified immunoglobulins can be readily designed and manufactured utilizing various recombinant DNA techniques well known to those skilled in the art. For example, the framework regions can vary from the native sequences at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis (see, Gillman and Smith, Gene 8, 81-97 (1979) and Roberts S. et al., Nature 328, 731-734 (1987), both of which are incorporated herein by reference.)

Alternatively, polypeptide fragments comprising only a portion of the primary antibody structure may be produced, which fragments possess one or more immunoglobulin activities (e.g., complement fixation activity). These polypeptide fragments may be produced by proteolytic cleavage of intact antibodies by methods well known in the art, or by inserting stop codons at the desired locations in the vectors using site-directed mutagenesis, such as after CH1 to produce Fab fragments or after the hinge region to produce $F(ab')_2$ fragments. Single chain antibodies may be produced by joining VL and VH with a DNA linker (see Huston et al., op cit., and Bird et al., op. cit.). Also because like many genes, the immunoglobulin-related genes contain separate functional regions, each having one or more distinct biological activities, the genes may be fused to functional regions from other genes to produce fusion proteins having novel properties.

As stated previously, the polynucleotides will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference). *E. coli* is one prokaryotic host useful particularly for cloning the polynucleotides of the present invention. Other microbial hosts suitable for use include bacilli, such as *Bacillus subtilus*, and other enterobacteriacea, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation. Other microbes, such as yeast, may also be used for expression. *Saccharomyces* is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention (see, Winnacker, *From Genes to Clones*, VCH Publishers, N.Y., N.Y. (1987), which is incorporated herein by reference). Eukaryotic cells are actually preferred, because a number of suitable host cell lines capable of secreting intact immunoglobulins have been developed in the art, and include the COS cell lines, various COS cell lines, HeLa cells, preferably myeloma cell lines, etc., or transformed B-cells of hybridomas. Expression vectors for these cells can include expression control sequences, such as an origin of replication, a promoter, and enhancer (Queen et al., Immunol. Rev. 89, 46-68 (1986), which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, cytomegalovirus and the like.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (See, generally, Maniatis et al., *Molecular Cloning: A Laboratory Manual*, Cold Spring Harbor Press (1982), which is incorporated herein by reference.)

Once expressed, the whole antibodies, their dimers, individual light and heavy chains, or other immunoglobulin forms of the present invention can be purified according to standard procedures in the art, including ammonium sulfate precipitation, affinity columns, column chromatography, gel electrophoresis and the like (see, generally, Scopes, R., *Protein Purification*, Springer-Verlag, N.Y. (1982), which is incorporated herein by reference). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally) or in developing and performing assay procedures, immunofluorescent stainings, and the like. (See, generally, *Immunological Methods*, Vols. I and II, Lefkovits and Pernis, eds., Academic Press, New York, N.Y. (1979 and 1981).

The immunoglobulins of the present invention will typically find use individually in treating thrombotic diseases in human patients. The humanized immunoglobulins and pharmaceutical compositions thereof of this invention are particularly useful for parenteral administration, i.e., subcutaneously, intramuscularly, intravenously or intraocularly. The compositions for parenteral administration will commonly comprise a solution of the immunoglobulin or a cocktail thereof dissolved in an acceptable carrier, preferably an aqueous carrier. A variety of aqueous carriers can be used, e.g., water, buffered water, 0.4% saline, 0.3% glycine, 5% glucose, human albumin solution and the like. These solutions are sterile and generally free of particulate matter. These compositions may be sterilized by conventional, well-known sterilization techniques. The compositions may contain pharmaceutically acceptable auxiliary substances as required to approximate physiological conditions such as pH adjusting and buffering agents, tonicity agents, toxicity adjusting agents and the like, for example sodium acetate, sodium chloride, potassium chloride, calcium chloride, sodium lactate, sodium citrate, etc. The concentration of immunoglobulin in these formulations can vary widely, i.e., from the less than about 0.5%, usually at least about 1% to as much a 15 or 20% by weight and will be selected primarily based on fluid volumes, viscosities, etc., in accordance with the particular mode of administration selected.

Thus, a typical pharmaceutical composition for injection could be made up to contain 1 ml sterile buffered water, and 1-100 mg of immunoglobulin. A typical composition for intravenous infusion could be made up to contain 250 ml of sterile Ringer's solution, and 150 mg of immunoglobulin. Actual methods for preparing parentally administrable compositions will be known or apparent to those skilled in the art and are described in more detail in, for example, *Remington's Pharmaceutical Science*, $15^{th}$ ed., Mack Publishing Company, Easton, Pa. (1980), which is incorporated herein by reference.

The immunoglobulins of this invention can be frozen or lyophilized for storage and reconstituted in a suitable carrier prior to use. This technique has been shown to be effective with conventional immunoglobulins and art-known lyophilization and reconstitution techniques can be employed. It will be appreciated by those skilled in the art that lyophilization and reconstitution can lead to varying degrees of immunoglobulin activity loss (e.g., with conventional immunoglobulins, IgM antibodies tend to have greater activity loss than IgG antibodies) and that use levels may have to be adjusted to compensate.

The compositions containing the present humanized immunoglobulins or a cocktail thereof can be administered for therapeutic or prophylactic treatments. In therapeutic application, compositions are administered to a patient already suffering from thrombotic disease in an amount sufficient to cure or at least partially arrest the disease and its complications without causing hemorrhage. An amount adequate to accomplish this is defined as a "therapeutically effective dose." Amounts effective for this use will depend upon the severity of the disease and the general state of the patient's own immune system, but generally range from about 0.1 to 200 mg/kg of immunoglobulin per patient dose being commonly used. Specific dosing regimens with doses of 1 mg/kg, 5 mg/kg, 10 mg/kg, 20 mg/kg, etc. administered daily, 2 or 3 per week, weekly, biweekly, monthly, etc. are all possible and would be selected by a skilled physician depending on the severity of the disease and other factors.

It must be kept in mind that the materials of this invention may generally be employed in serious disease states, that is, life-threatening or potentially life-threatening situations. In such cases, in view of the minimization of extraneous substances and the lower probability of "foreign substance" rejections which are achieved by the present humanized immunoglobulins of this invention, it is possible and may be felt desirable by the treating physician to administer substantial excesses of these immunoglobulins.

Single or multiple administrations of the compositions can be carried out with dose levels and pattern being selected by the treating physician. In any event, the pharmaceutical formulations should provide a quantity of the immunoglobulin(s) of this invention sufficient to effectively treat the patient.

In particular embodiments, compositions comprising humanized immunoglobulins of the present invention may be used to detect vWF. Thus, a humanized immunoglobulin that binds to the antigen determinant identified by the AJvW-2 antibody may be labeled and used to identify anatomic sites that contain significant concentrations of vWF. For example but not for limitation, one or more labeling moieties may be attached to the humanized immunoglobulin. Exemplary labeling moieties include, but are not limited to, radiopaque dyes, radiocontrast agents, fluorescent molecules, spin-labeled molecules, enzymes, or other labeling moieties of diagnostic value, particularly in radiologic or magnetic resonance imaging techniques.

Humanized immunoglobulins of the present invention can further find a wide variety of uses in vitro. By way of example, the immunoglobulins can be used for detection of vWF.

For diagnostic purposes, the immunoglobulins may either be labeled or unlabeled. Unlabeled immunoglobulins can be used in combination with other labeled antibodies (second antibodies) that are reactive with the humanized immunoglobulin, such as antibodies specific for human immunoglobulin constant regions. Alternatively, the immunoglobulins can be directly labeled. A wide variety of labels may be employed, such as radionuclides, fluors, enzymes, enzyme substrates, enzyme cofactors, enzyme inhibitors, ligands (particularly haptens), etc. Numerous types of immunoassays are available and are well known to those skilled in the art.

Kits can also be supplied for use with the subject immunoglobulins in the protection against or detection of a cellular activity or for the presence of a selected antigen. Thus, the subject immunoglobulin composition of the present invention may be provided, usually in a lyophilized form in a container, either alone or in conjunction with additional antibodies specific for the desired cell type. The immunoglobulins, which may be conjugated to a label or toxin, or unconjugated, are included in the kits with buffers, such as Tris, phosphate, carbonate, etc., stabilizers, preservatives, biocides, inert proteins, e.g., serum albumin, or the like, and a set of instructions for use. Generally, these materials will be present in less than about 5% wt. based on the amount of active immunoglobulin, and usually present in total amount of at least about 0.001% wt., based again on the immunoglobulin concentration. Frequently, it will be desirable to include an inert extender or excipient to dilute the active ingredients, where the excipient may be present in from about 1 to 99% wt. of the total composition. Where a second antibody capable of binding to the immunoglobulin is employed in an assay, this will usually be present in a separate vial. The second antibody is typically conjugated to a label and formulated in an analogous manner with the immunoglobulin formulations described above.

The following examples are offered by way of illustration, not by limitation. It will be understood that although the examples pertain to the humanized AJvW-2 antibody, producing humanized antibodies with high binding affinity for the vWF antigen it is also contemplated using CDR's from other monoclonal antibodies that bind to the same epitope of vWF.

EXAMPLES

Example 1

Cloning and Sequencing of Mouse AJvW-2 Variable Region cDNAs

Mouse AJvW-2 heavy and light chain variable region cDNAs were cloned from mRNA isolated from hybridoma cells using anchored PCR (Co et al., *J Immunol.* 148: 1149 (1992)). The 5' primers that were used annealed to poly-dG tails added to the cDNA, and the 3' primers to the constant regions. The amplified gene fragments were then inserted into the plasmid pUC18. Nucleotide sequences were determined from several independent clones for both $V_L$ and $V_H$ cDNA. For the heavy chain, a single, unique sequence was identified, typical of a mouse heavy chain variable region. For the light chain, two unique sequences, both homologous to murine light chain variable region sequences, were identified. However, one sequence was not functional because of a missing nucleotide that caused a frame shift at the V-J junction, and was identified as the non-productive allele. The other sequence was typical of a functional mouse kappa chain variable region. The variable region cDNA sequences of the heavy chain and the functional light chain and the translated amino acid sequences are shown in FIG. 1. The mouse $V_K$ sequence belongs to Kabat's mouse kappa chain subgroup V. The mouse $V_H$ belongs to Kabat's heavy chain subgroup III(B).

Example 2

Design of Humanized AJvW-2 Variable Regions

To retain the binding affinity of the mouse antibody in the humanized antibody, the general procedures of Queen et al. were followed (Queen et al. *Proc. Natl. Acad. Sci. USA* 86: 10029 (1989) and U.S. Pat. Nos. 5,585,089 and 5,693,762).

The choice of framework residues can be critical in retaining high binding affinity. In principle, a framework sequence from any human antibody can serve as the template for CDR grafting; however, it has been demonstrated that straight CDR replacement into such a framework can lead to significant loss of binding affinity to the antigen (Tempest et al., *Biotechnology* 9: 266 (1992); Shalaby et al., *J. Exp. Med.* 17: 217 (1992)). The more homologous a human antibody is to the original murine antibody, the less likely will the human framework introduce distortions into the mouse CDRs that could reduce affinity. Based on a sequence homology search against the Kabat database (Kabat et al., Sequences of Proteins of Immunological Interest, 5th ed., U.S. Department of Health and Human Services, 1991), the human antibody I3R was chosen as providing good framework homology to the mouse AJvW-2 antibody. Other highly homologous human antibody chains would also be suitable to provide the humanized antibody framework, especially kappa light chains from human subgroup I and heavy chains from human subgroup III as defined by Kabat.

The computer programs ABMOD and ENCAD (Zilber et al., *Biochemistry*, Vol. 29, 10032 (1990); Levitt et al., *J. Mol. Biol.* 168: 595 (1983)) were used to construct a molecular model of the AJvW-2 variable domain, which was used to locate the amino acids in the AJvW-2 framework that are close enough to the CDRs to potentially interact with them. To design the humanized AJvW-2 heavy and light chain variable regions, the CDRs from the mouse AJvW-2 antibody were grafted into the framework regions of the human I3R antibody. At framework positions where the computer model suggested significant contact with the CDRs, the amino acids from the mouse antibody were substituted for the original human framework amino acids. For humanized AJvW-2, this was done at residues 28, 48, 49 and 67 of the heavy chain and at residues 48, 70 and 71 of the light chain. Furthermore, framework residues that occurred only rarely at their positions in the database of human antibodies were replaced by a human consensus amino acid at those positions. For humanized AJvW-2 this was done at residues 1, 78 and 118 of the heavy chain and at residues 62, 73 and 83 of the light chain.

The sequences of the humanized AJvW-2 antibody heavy chain and light chain variable regions are shown in FIG. 2. However, many of the potential CDR-contact residues are amenable to substitution by other amino acids and still allow the antibody to retain substantial affinity for the antigen. The following table lists a number of positions in the framework where alternative amino acids are suitable (LC=light chain, HC=heavy chain).

TABLE I

| Position | Humanized AJvW-2 | Alternatives |
|---|---|---|
| LC-48 | V | I |
| LC-70 | Q | D |
| LC-71 | Y | F |
| HC-28 | D | T |
| HC-48 | I | V |
| HC-49 | G | A, S |
| HC-67 | K | R |

Likewise, many of the framework residues not in contact with the CDRs in the humanized AJvW-2 heavy and light chains can accommodate substitutions of amino acids from the corresponding positions of the human I3R antibody, from other human antibodies, by human consensus amino acids, from the mouse AJvW-2 antibody, or from other mouse antibodies, without significant loss of the affinity or non-immunogenicity of the humanized antibody. The following table lists a number of additional positions in the framework where alternative amino acids may be suitable.

TABLE 2

| Position | Humanized AJvW-2 | Alternatives |
|---|---|---|
| LC-62 | F | I |
| LC-73 | L | F |
| LC-83 | F | I |
| HC-1 | E | Q |
| HC-78 | T | S |
| HC-118 | T | I, S |

Selection of various alternative amino acids may be used to produce versions of humanized AJvW-2 that have varying combinations of affinity, specificity, non-immunogenicity, ease of manufacture, and other desirable properties. Thus, the examples in the above tables are offered by way of illustration, not of limitation.

Example 3

Construction of Humanized AJvW-2

Once the humanized variable region amino acid sequences had been designed as described above, genes were constructed to encode them, including signal peptides, splice donor signals and appropriate restriction sites (FIG. 2). The light and heavy chain variable region genes were constructed and amplified using eight overlapping synthetic oligonucleotides ranging in length from approximately 65 to 80 bases (see He et al. *J. Immunol.* 160: 1029 (1998)). The oligos were annealed pairwise and extended with the Klenow fragment of DNA polymerase I, yielding four double-stranded fragments. The resulting fragments were denatured, annealed, and extended with Klenow, yielding two fragments. These fragments were denatured, annealed pairwise, and extended once again, yielding a full-length gene. The resulting product was amplified by polymerase chain reaction (PCR) using Taq polymerase, gel-purified, digested with XbaI, gel-purified again, and subcloned into the XbaI site of the pVk, pVg4 or pVg2.M3 expression vector. The pVk vector for light chain expression has been previously described (see Co et al., *J. Immunol.* 148:1149 (1992)). The pVg4 vector for heavy chain expression was constructed by replacing the XbaI-BamHI fragment of pVg1 containing the g1 constant region gene (see Co et al., *J. Immunol.* 148: 1149 (1992)) with an approximately 2000 bp fragment of the human g4 constant region gene (Ellison and Hood, *Proc. Natl. Acad. Sci. USA* 79: 1984 (1982)) that extended from the HindIII site preceding the $C_H1$ exon of the g4 gene to 270 bp after the NsiI site following the $C_H4$ exon of the gene. The pVg2.M3 vector for expression of gamma 2 chain has been previously described (see Cole, et al., *J. Immunol.* 159: 3613 (1997)). The pVg2.M3 is a variant of the human wildtype IgG2 by replacing the amino acids Val and Gly at positions 234 and 237 with Ala. The variant has a reduced interaction with its Fc receptors and thus has minimal antibody effector activity.

The structure of the final plasmids were verified by nucleotide sequencing and restriction mapping. All DNA manipulations were performed by standard methods well-known to those skilled in the art.

Two humanized AJvW-2, an IgG4 and an IgG2.M3, were generated for comparative studies. To construct a cell line producing humanized AJvW-2, the respective heavy chain and light chain plasmids were transfected into the mouse myeloma cell line Sp2/0-Ag14 (ATCC CRL 1581). Before transfection, the heavy and light chain-containing plasmids were linearized using restriction endonucleases. The kappa chain and the gamma2 heavy chain were linearized using FspI; the gamma 4 chain was linearized using BstZ17I. Approximately 20 μg of each plasmid was transfected into $1\times10^7$ cells in PBS. Transfection was by electroporation using a Gene Pulser apparatus (BioRad) at 360 V and 25 μFD capacitance according to the manufacturer's instructions. The cells from each transfection were plated in four 96-well tissue culture plates, and after two days, selection medium (DMEM, 10% FCS, 1×HT supplement (Sigma), 0.25 mg/ml xanthine, 1 μg/ml mycophenolic acid) was applied.

After approximately two weeks, the clones that appeared were screened for antibody production by ELISA. Antibody from a high-producing clone was prepared by growing the cells to confluency in regular medium (DMEM with 10% FCS), then replacing the medium with a serum-free medium (Hybridoma SMF; Gibco) and culturing until maximum antibody titers were achieved in the culture. The culture supernatant was run through a protein A-Sepharose column (Pharmacia); antibody was eluted with 0.1 M Glycine, 100 mM NaCl, pH 3, neutralized and subsequently exchanged into phosphate-buffered saline (PBS). The purity of the antibody was verified by analyzing it on an acrylamide gel, and its concentration was determiined by an $OD_{280}$ reading, assuming 1.0 mg of antibody protein has an $OD_{280}$ reading of 1.4.

Example 4

Properties of Humanized AJvW-2

The affinity of the murine and humanized AJvW-2 antibodies for von Willebrand factor (vWF) was determined by competitive binding with biotinylated murine AJvW-2 antibody. The procedure for the experiment is described below:

1. vWF solution was diluted to 8 ug/ml with TBS (20 mM Tris pH 7.4+0.15 M NaCl). 50 ul was dispensed to each well of a 96-well NUNC Maxisorp plate (VWR Scientific Product) and incubated overnight at 4° C.
2. The plate was washed once with TBS, blocked by adding 200 ul/well of a blocking solution (TBS+5% BSA) and incubated for 3 hr at room temperature.
3. The plate was washed three times with TBS.
4. Murine AJvW-2 was previously biotinylated using sulfo-succinimidyl-6-(biotinamido)hexanoate (Pierce, Rockford, Ill., product number 21335) according to the manufacturer's instruction. The biotinylated antibody was diluted to 0.5 ug/ml in TBS+0.1% BSA.
5. Eight 4-fold serial dilutions of cold competitor murine and humanized antibodies were prepared in TBS+0.1% BSA, starting at 25 ug/ml.
6. The following solutions were added to each well of the vWF coated plate: 25 ul TBS+1% BSA+10% DMSO, 100 ul of cold competitor antibody (murine, humanized IgG2m3 or humanized IgG4) and 25 ul of biotinylated antibody, and incubate at room temperature for 1 hr with gentle shaking.
7. The plate was washed three times with a washing solution (TBS+0.05% Tween-20) and stained with the ImmunoPure ABC Phosphatase Staining Kits (Pierce, Rockford, Ill.) according to the manufacturer's instruction. Specifically, a solution was prepared by adding 2 drops of reagent A (avidin) and 2 drops of reagent B (biotinylated alkaline phosphatase) to 50 ml of TBS+0.1% BSA. 50 ul of the prepared solution was added to each well of the 96-well plate and incubated at room temperature for 1 hr.
8. The plate was washed three times with the washing solution and developed with Alkaline Phosphatase substrate (Sigma, St. Louis, Mo.).
9. Absorbance was measured at 405 nm and plotted against the concentration of competitor antibodies.

The result, shown in FIG. 3, demonstrated that the humanized AJvW-2 IgG4 and IgG2m3 compete equally well with the biotinylated murine antibody when compared to the unlabeled murine antibody, suggesting that the two humanized antibodies have similar binding affinities and there is no significant difference in the affinity of the humanized antibodies and the murine antibody to the antigen.

FIG. 1 shows the cDNA and translated amino acid sequences of the heavy chain (A) and light chain (B) variable regions of the murine AJvW-2 antibody. The complementarity determining regions (CDRs) are underlined and the first amino acids of the mature chains are double underlined.

FIG. 2 shows the DNA and translated amino acid sequences of the heavy chain (A) and light chain (B) variable regions of the humanized AJvW-2 antibody. The complementarity determining regions (CDRs) are underlined and the first amino acids of the mature chains are double underlined.

FIG. 3 is a graph of competitive binding properties of murine and humanized AJvW-2 antibodies (IgG4 and IgG2m3) to von Willebrand factor. Increasing concentrations of cold competitor antibody were incubated with von Willebrand factor in the presence of biotinylated tracer murine AJvW-2. Absorbance was measured and plotted against the concentration of the unlabeled competitor antibodies.

Obviously numerous variations of the invention are possible in light of the above teachings. Therefore, within the scope of the appended claims, the invention may be practiced otherwise than as specifically described.

We claim:

1. A method of treating a patient having or at risk of a thrombotic disease or atherosclerosis, comprising: administering to said patient an effective dose of a humanized immunoglobulin, wherein said humanized immunoglobulin binds to the von Willebrand factor and inhibits the binding of the von Willebrand factor to the GPIb protein and said humanized immunoglobulin comprises (a) complementarity determining regions comprising amino acid sequences RFWMS, residues 49-53 of SEQ ID NO: 6, EVNPDNNTMNYTPSLKD, residues 68-84 of SEQ ID NO: 6, and PPYYGSYGGFAY, residues 117-128 of SEQ ID NO: 6, in the heavy chain (HC), and RASENIYNNLA, residues 44-54 of SEQ ID NO: 8, AATNLAD, residues 70-76 of SEQ ID NO: 8 and GHLWTSPYT, residues 109-117 of SEQ ID NO: 8, in the light chain (LC), and (b) framework regions of human antibody, wherein the framework regions of a human antibody correspond to residues 21-43, 55-69, 77-108, and 118-127 of SEQ ID NO: 8 for the light and to residues 19-48, 54-67, 85-116, and 119-139 of SEQ ID NO: 6 for the heavy chain, and wherein at least one amino acid selected from the group consisting of LC-48, residue 68 of SEQ ID NO: 8, LC-70, residue 90 of SEQ ID NO: 8, LC-71, residue 91 of SEQ ID NO: 8, HC-28, residue 46 of SEQ ID NO: 6, HC-48, residue 66 of SEQ ID NO: 6, HC-49, residue 67 of SEQ ID NO: 6, and HC-67, residue 85 of SEQ ID NO: 6, is replaced with an amino acid present in the equivalent position of a mouse AJvW-2 antibody heavy or light chain variable region framework.

2. The method of claim 1, wherein the treatment is for stroke, transient ischemic attack, unstable angina, acute myocardial infarction, peripheral vascular disease, deep vein thrombosis, hemolytic uremic syndrome, hemolytic anemia, acute renal failure, thrombotic thrombocytopenic purpura, ischemic complications caused by acute and subacute thrombosis, or restenosis after endovascular intervention.

3. The method of claim 1, wherein the immunoglobulin is a Fab, a $F(ab')_2$, or a Fv.

4. The method of claim 1, wherein the immunoglobulin is a single chain antibody.

5. The method of claim 1, wherein the immunoglobulin has an $IgG_2$ or $IgG_4$ immunoglobulin subtype.

6. The method of claim 1, wherein the immunoglobulin is admixed with a pharmaceutically acceptable carrier.

7. The method of claim 1 , wherein said administering is parenteral.

8. The method of claim 1, wherein said administering is subcutaneous.

9. The method of claim 1, wherein said administering is intramuscular.

10. The method of claim 1, wherein said administering is intravenous.

11. The method of claim 1, wherein said administering is intraocular.

12. The method of claim 1, wherein said effective dose ranges from 0.1 to 200 mg of humanized immunoglobulin per 1 kg of patient weight.

* * * * *

SEQUENCE LISTING

```
<160> NUMBER OF SEQ ID NOS: 8

<210> SEQ ID NO 1
<211> LENGTH: 417
<212> TYPE: DNA
```

-continued

```
<213> ORGANISM: Mus musculus
<220> FEATURE:
<221> NAME/KEY: CDS
<222> LOCATION: (1)..(417)
<223> OTHER INFORMATION:

<400> SEQUENCE: 1

atg gat ttt ggg ctg att ttt ttt att gtt gct ctt tta aaa ggg gtc       48
Met Asp Phe Gly Leu Ile Phe Phe Ile Val Ala Leu Leu Lys Gly Val
1               5                   10                  15

cag tgt gag gtg aaa ctt ctc gag tct gga ggt ggc ctg gtg cag act       96
Gln Cys Glu Val Lys Leu Leu Glu Ser Gly Gly Gly Leu Val Gln Thr
            20                  25                  30

gga gga tcc ctg aaa ctc tcc tgt gca gcc tca gga ttc gat ttt agt      144
Gly Gly Ser Leu Lys Leu Ser Cys Ala Ala Ser Gly Phe Asp Phe Ser
        35                  40                  45

aga ttc tgg atg agt tgg gtc cgg cag gct cca ggg aaa ggg cta gaa      192
Arg Phe Trp Met Ser Trp Val Arg Gln Ala Pro Gly Lys Gly Leu Glu
    50                  55                  60

tgg att gga gaa gtt aat cca gat aac aat acg atg aac tat acg cca      240
Trp Ile Gly Glu Val Asn Pro Asp Asn Asn Thr Met Asn Tyr Thr Pro
65                  70                  75                  80

tct cta aag gat aaa ttc atc atc tcc aga gac aac gcc aaa aat acg      288
Ser Leu Lys Asp Lys Phe Ile Ile Ser Arg Asp Asn Ala Lys Asn Thr
                85                  90                  95

ctg tac ctg caa atg agt caa gtg aga tct gag gac aca gcc ctt tac      336
Leu Tyr Leu Gln Met Ser Gln Val Arg Ser Glu Asp Thr Ala Leu Tyr
            100                 105                 110

tac tgt gca aga cct ccc tac tat ggt agc tac ggg ggg ttt gct tac      384
Tyr Cys Ala Arg Pro Pro Tyr Tyr Gly Ser Tyr Gly Gly Phe Ala Tyr
        115                 120                 125

tgg ggc caa ggg act ctg gtc tct gtc tcg cca                          417
Trp Gly Gln Gly Thr Leu Val Ser Val Ser Pro
    130                 135


<210> SEQ ID NO 2
<211> LENGTH: 139
<212> TYPE: PRT
<213> ORGANISM: Mus musculus

<400> SEQUENCE: 2

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Thr
            20                  25                  30

Gly Gly Ser Leu Lys Leu Ser Cys Ala Ala Ser Gly Phe Asp Phe Ser
        35                  40                  45

Arg Phe Trp Met Ser Trp Val Arg Gln Ala Pro Gly Lys Gly Leu Glu
    50                  55                  60

Trp Ile Gly Glu Val Asn Pro Asp Asn Asn Thr Met Asn Tyr Thr Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Gln Val Arg Ser Glu Asp Thr Ala Leu Tyr
            100                 105                 110

Tyr Cys Ala Arg Pro Pro Tyr Tyr Gly Ser Tyr Gly Gly Phe Ala Tyr
        115                 120                 125

Trp Gly Gln Gly Thr Leu Val Ser Val Ser Pro
    130                 135
```

-continued

<210> SEQ ID NO 3
<211> LENGTH: 381
<212> TYPE: DNA
<213> ORGANISM: Mus musculus
<220> FEATURE:
<221> NAME/KEY: CDS
<222> LOCATION: (1)..(381)
<223> OTHER INFORMATION:

<400> SEQUENCE: 3

```
atg agt gtg ccc act cag gtc ctg ggg ttg ctg ctg ctg tgg ctt aca       48
Met Ser Val Pro Thr Gln Val Leu Gly Leu Leu Leu Leu Trp Leu Thr
1               5                   10                  15

gat gcc aga tgt gac atc cag atg act cag tct cca gcc tcc cta tct       96
Asp Ala Arg Cys Asp Ile Gln Met Thr Gln Ser Pro Ala Ser Leu Ser
            20                  25                  30

gta tct gtg gga gaa act gtc acc atc aca tgt cga gca agt gag aat      144
Val Ser Val Gly Glu Thr Val Thr Ile Thr Cys Arg Ala Ser Glu Asn
        35                  40                  45

att tac aat aat tta gct tgg tat cag cag aga cag gga aaa tct cct      192
Ile Tyr Asn Asn Leu Ala Trp Tyr Gln Gln Arg Gln Gly Lys Ser Pro
    50                  55                  60

cag ctc ctg gtc tat gct gca aca aac tta gca gat ggt gtg cca tca      240
Gln Leu Leu Val Tyr Ala Ala Thr Asn Leu Ala Asp Gly Val Pro Ser
65                  70                  75                  80

agg ttc agt ggc agt gga tca ggc aca cag tat tcc ctc aag atc gac      288
Arg Phe Ser Gly Ser Gly Ser Gly Thr Gln Tyr Ser Leu Lys Ile Asp
                85                  90                  95

agc ctg cag tct gaa gat ttt ggg agt tat tac tgt caa cat ttg tgg      336
Ser Leu Gln Ser Glu Asp Phe Gly Ser Tyr Tyr Cys Gln His Leu Trp
            100                 105                 110

act tct ccg tac acg ttc gga ggg ggg acc aag ctg gaa ata aaa          381
Thr Ser Pro Tyr Thr Phe Gly Gly Gly Thr Lys Leu Glu Ile Lys
        115                 120                 125
```

<210> SEQ ID NO 4
<211> LENGTH: 127
<212> TYPE: PRT
<213> ORGANISM: Mus musculus

<400> SEQUENCE: 4

```
Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ala Ser Leu Ser
            20                  25                  30

Val Ser Val Gly Glu Thr Val Thr Ile Thr Cys Arg Ala Ser Glu Asn
        35                  40                  45

Ile Tyr Asn Asn Leu Ala Trp Tyr Gln Gln Arg Gln Gly Lys Ser Pro
    50                  55                  60

Gln Leu Leu Val Tyr Ala Ala Thr Asn Leu Ala Asp Gly Val Pro Ser
65                  70                  75                  80

Arg Phe Ser Gly Ser Gly Ser Gly Thr Gln Tyr Ser Leu Lys Ile Asp
                85                  90                  95

Ser Leu Gln Ser Glu Asp Phe Gly Ser Tyr Tyr Cys Gln His Leu Trp
            100                 105                 110

Thr Ser Pro Tyr Thr Phe Gly Gly Gly Thr Lys Leu Glu Ile Lys
        115                 120                 125
```

<210> SEQ ID NO 5
<211> LENGTH: 417

-continued

<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(417)
<223> OTHER INFORMATION:

<400> SEQUENCE: 5

```
atg gat ttt ggg ctg att ttt ttt att gtt gct ctt tta aaa ggg gtc       48
Met Asp Phe Gly Leu Ile Phe Phe Ile Val Ala Leu Leu Lys Gly Val
1               5                   10                  15

cag tgt gag gtg caa ctt gtc gag tct gga ggt gga cta gtg cag cct       96
Gln Cys Glu Val Gln Leu Val Glu Ser Gly Gly Gly Leu Val Gln Pro
            20                  25                  30

gga gga tca ctg aga ctc tcc tgt gca gcc tca gga ttc gat ttt agt      144
Gly Gly Ser Leu Arg Leu Ser Cys Ala Ala Ser Gly Phe Asp Phe Ser
        35                  40                  45

aga ttc tgg atg agt tgg gtc cgg cag gct cca ggg aaa ggg ctc gag      192
Arg Phe Trp Met Ser Trp Val Arg Gln Ala Pro Gly Lys Gly Leu Glu
    50                  55                  60

tgg att gga gaa gtt aat cca gat aac aat acg atg aac tat acg cca      240
Trp Ile Gly Glu Val Asn Pro Asp Asn Asn Thr Met Asn Tyr Thr Pro
65                  70                  75                  80

tct cta aag gat aaa ttc acc atc tcc aga gac aac gcc aaa aat acg      288
Ser Leu Lys Asp Lys Phe Thr Ile Ser Arg Asp Asn Ala Lys Asn Thr
                85                  90                  95

ctg tac ctg caa atg aac tca ttg aga gct gag gac acg gcc gtt tac      336
Leu Tyr Leu Gln Met Asn Ser Leu Arg Ala Glu Asp Thr Ala Val Tyr
            100                 105                 110

tac tgt gca aga cct ccc tac tat ggt agc tac ggg ggg ttt gct tac      384
Tyr Cys Ala Arg Pro Pro Tyr Tyr Gly Ser Tyr Gly Gly Phe Ala Tyr
        115                 120                 125

tgg ggc caa ggg act ctg gtc acc gtc tcc tca                          417
Trp Gly Gln Gly Thr Leu Val Thr Val Ser Ser
    130                 135
```

<210> SEQ ID NO 6
<211> LENGTH: 139
<212> TYPE: PRT
<213> ORGANISM: Artificial Sequence
<220> FEATURE:
<223> OTHER INFORMATION: Synthetic Peptide

<400> SEQUENCE: 6

```
Met Asp Phe Gly Leu Ile Phe Phe Ile Val Ala Leu Leu Lys Gly Val
1               5                   10                  15

Gln Cys Glu Val Gln Leu Val Glu Ser Gly Gly Gly Leu Val Gln Pro
            20                  25                  30

Gly Gly Ser Leu Arg Leu Ser Cys Ala Ala Ser Gly Phe Asp Phe Ser
        35                  40                  45

Arg Phe Trp Met Ser Trp Val Arg Gln Ala Pro Gly Lys Gly Leu Glu
    50                  55                  60

Trp Ile Gly Glu Val Asn Pro Asp Asn Asn Thr Met Asn Tyr Thr Pro
65                  70                  75                  80

Ser Leu Lys Asp Lys Phe Thr Ile Ser Arg Asp Asn Ala Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Pro Pro Tyr Tyr Gly Ser Tyr Gly Gly Phe Ala Tyr
```

-continued

```
        115                 120                 125

Trp Gly Gln Gly Thr Leu Val Thr Val Ser Ser
    130                 135


<210> SEQ ID NO 7
<211> LENGTH: 381
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(381)
<223> OTHER INFORMATION:

<400> SEQUENCE: 7

atg agt gtg ccc act cag gtc ctg ggg ttg ctg ctg ctg tgg ctt aca       48
Met Ser Val Pro Thr Gln Val Leu Gly Leu Leu Leu Leu Trp Leu Thr
1               5                   10                  15

gat gcc aga tgt gac atc cag atg act cag tct cca tcc tcc cta tct       96
Asp Ala Arg Cys Asp Ile Gln Met Thr Gln Ser Pro Ser Ser Leu Ser
            20                  25                  30

gca tct gtg gga gac agg gtc acc atc aca tgt cga gca agt gag aat      144
Ala Ser Val Gly Asp Arg Val Thr Ile Thr Cys Arg Ala Ser Glu Asn
        35                  40                  45

att tac aat aat tta gct tgg tat cag cag aaa ccg gga aaa gct cct      192
Ile Tyr Asn Asn Leu Ala Trp Tyr Gln Gln Lys Pro Gly Lys Ala Pro
    50                  55                  60

aag cta cta gtc tat gct gca aca aac tta gca gat ggt gtg cca tca      240
Lys Leu Leu Val Tyr Ala Ala Thr Asn Leu Ala Asp Gly Val Pro Ser
65                  70                  75                  80

agg ttc agt ggc agt gga tca ggc aca cag tat acc ctc acg atc agc      288
Arg Phe Ser Gly Ser Gly Ser Gly Thr Gln Tyr Thr Leu Thr Ile Ser
                85                  90                  95

agc ctc cag cct gag gat ttt gcg act tat tac tgt caa cat ttg tgg      336
Ser Leu Gln Pro Glu Asp Phe Ala Thr Tyr Tyr Cys Gln His Leu Trp
            100                 105                 110

act tct ccg tac acg ttc gga ggg ggg acc aag gtg gaa ata aaa          381
Thr Ser Pro Tyr Thr Phe Gly Gly Gly Thr Lys Val Glu Ile Lys
        115                 120                 125


<210> SEQ ID NO 8
<211> LENGTH: 127
<212> TYPE: PRT
<213> ORGANISM: Artificial Sequence
<220> FEATURE:
<223> OTHER INFORMATION: Synthetic Peptide

<400> SEQUENCE: 8

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Glu Asn
        35                  40                  45

Ile Tyr Asn Asn Leu Ala Trp Tyr Gln Gln Lys Pro Gly Lys Ala Pro
    50                  55                  60

Lys Leu Leu Val Tyr Ala Ala Thr Asn Leu Ala Asp Gly Val Pro Ser
65                  70                  75                  80

Arg Phe Ser Gly Ser Gly Ser Gly Thr Gln Tyr Thr Leu Thr Ile Ser
                85                  90                  95
```

-continued

```
Ser Leu Gln Pro Glu Asp Phe Ala Thr Tyr Tyr Cys Gln His Leu Trp
            100                 105                 110

Thr Ser Pro Tyr Thr Phe Gly Gly Gly Thr Lys Val Glu Ile Lys
        115                 120                 125
```